United States Patent [19]

De Witt et al.

[11] 4,343,947
[45] Aug. 10, 1982

[54] CARNITINAMIDES OF OPTICALLY ACTIVE AMINOACIDS

[75] Inventors: Paolo De Witt; Maria O. Tinti, both of Rome, Italy

[73] Assignee: Sigma-Tau Industrie Farmaceutiche Riunite S.p.A., Rome, Italy

[21] Appl. No.: 220,492

[22] Filed: Dec. 29, 1980

[30] Foreign Application Priority Data

Jan. 29, 1980 [IT] Italy ............................... 47749 A/80

[51] Int. Cl.³ ................. C07D 233/58; C07C 101/30; C07C 101/32; C07C 101/26
[52] U.S. Cl. ..................................... 548/344; 560/39; 560/40; 560/169; 560/153
[58] Field of Search .................. 560/39, 40, 169, 153; 548/344

[56] References Cited

U.S. PATENT DOCUMENTS 3,265,719  8/1966  Cowen et al. ............... 560/169
3,979,441  9/1976  Hoke ........................... 560/169
4,116,962  9/1978  Ondetti et al. .............. 560/153
4,252,802  2/1981  Denzel et al. ............... 424/246

Primary Examiner—John M. Ford
Attorney, Agent, or Firm—Ladas & Parry

[57] ABSTRACT

Amides of carnitine or acyl-carnitines having general formula:

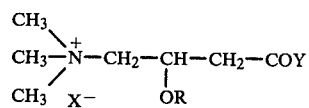

wherein
$X^-$ is a halogen anion, e.g. the chloride anion
R is either hydrogen or an acyl radical, such as acetyl, propionyl or butyryl; and
Y is the residue of an optically active esterified aminoacid (e.g. the residue of L-phenylglycine methyl ester,

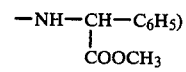

are prepared by either (a) directly condensing D,L-carnitine (or acyl-D,L-carnitine) with an ester of an optically active aminoacid, or (b) preparing the acid halogenide of D,L-carnitine or acyl-D,L-carnitine and subsequently condensing it with an ester of an optically active aminoacid.

The mixture of the diastereoisomer amides thus obtained is resolved by fractional crystallization from organic solvents into the respective separated diastereoisomers.

These optically active amides are useful therapeutic agents for treating cardiac disorders, hyperlipidaemias and hyperlipoproteinaemias and, furthermore, can be hydrolyzed with procedures known per se into L-carnitine and D-carnitine, respectively.

3 Claims, No Drawings

CARNITINAMIDES OF OPTICALLY ACTIVE AMINOACIDS

The present invention relates to a novel class of carnitine and acyl-carnitine amides, the processes for their preparation and their utilization as both therapeutic agents and intermediates in the optical antipode resolution for obtaining L-carnitine hydrochloride and D-carnitine hydrochloride.

More specifically, the present invention relates to carnitine and acyl-carnitine amides, wherein the amide residue is derived from an optically active, esterified amino-acid, these amides being represented by the general formula:

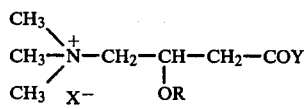

wherein:

$X^-$ is a halogen anion, preferably $Cl^-$;

R is either hydrogen or acyl group, preferably acetyl, propionyl, butyryl;

Y is the residue of an optically active, esterified amino-acid, having general formula:

$$-NH-CHR_1$$
$$\quad\quad |$$
$$\quad\quad COOR_2$$

wherein $R_1$ is:
—$CH_2COOR_2$
—$(CH_2)_2COOR_2$
—$CH_2S_2CH_2CH(NH_2)COOR_2$
—$CH_3$
—$CH(CH_3)_2$
—$CH_2CH(CH_3)_2$
—$CH(CH_3)CH_2CH_3$
—$(CH_2)_2SCH_3$
—$C_6H_5$
—$CH_2C_6H_5$
—$CH_2CONH_2$
—$(CH_2)_2CONH_2$

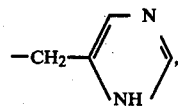

and $R_2$ is:
an alkyl radical of 1–4 carbon atoms, preferably methyl, ethyl or isopropyl.

It should be understood that the amides of this invention represented by formula (I) comprise both the mixtures of diastereoisomers and the separated optical antipodes which can be obtained from the mixtures with procedures which will be hereinbelow described.

Particularly preferred amides of general formula (I) are those amides wherein the amide residue is the residue of the methyl, ethyl or isopropyl diester of L-aspartic and L-glutamic acid, and of L-cystine; the residue of the methyl or ethyl ester of L-asparagine, L-phenyl alanine, L-glutamine, L-phenylglycine, L-leucine, L-isoleucine, L-methionine, L-histidine, L-valine and L-alanine.

The amides of formula (I) are prepared starting from D,L-carnitine hydrochloride or an acyl-D,L-carnitine hydrochloride, respectively, which for semplicity sake will be hereinbelow referred to as "carnitine" and "acyl-carnitine", respectively.

According to the invention, the amides of formula (I) are prepared by following two distinct synthesis routes, depending on whether carnitine or the acyl-carnitine is converted into the corresponding acid halogenide and this last compound is condensed with the desired ester of optically active amino-acid (Process A), or carnitine or the acyl-carnitine is directly condensed with the ester of optically active amino-acid in the presence of a suitable condensing agent (Process B).

More specifically, process A comprises the following steps:

(a) reacting carnitine or acyl-carnitine hydrochloride with an excess of a halogenating agent at about 25°–60° C. for about 0.3–24 hours and removing the halogenating agent excess thus obtaining the corresponding acid halogenide of carnitine or acyl-carnitine;

(b) dissolving the acid halogenide or carnitine or acyl-carnitine of step (a) in an inert anhydrous solvent;

(c) condensing said acid halogenide of carnitine or acyl-carnitine with an optically active amino-acid esterified with lower alkyl alcohols having from 1 to 4 carbon atoms dissolved in an inert anhydrous solvent, keeping under stirring the resulting mixture at room temperature, for about 3–48 hours, thus obtaining the amide of formula (I) (mixture of diastereoisomers); and (d) isolating the amide of formula (I), by concentrating the mixture of step (c) and purifying by repeated crystallizations.

Process B comprises the following steps:

(a') condensing carnitine or acyl-carnitine in aqueous solution with an optically active amino-acid esterified with lower alkyl alcohols having from 1 to 4 carbon atoms in a solution of organic solvents, such as acetone and dioxane, in the presence of a dicyclohexylcarbodiimide solution in the same organic solvent, keeping under stirring the mixture thus obtained at 15°–40° C. for 20–48 hours, thus obtaining the amide of formula (I) (diastereoisomer mixture) and a dicyclohexyl urea precipitate, and (b') filtering off the dicyclohexyl urea precipitate and isolating the amide of formula (I) by concentrating the filtrate, drying and repeatedly crystallizing from organic solvents.

The organic solvent of step (b') is preferably acetone. The molar ratio carnitine (or acyl-carnitine): ester of optically active amino-acid: dicyclohexylcarbodiimide is preferably 1:1:2.

The previously mentioned ester of optically active amino-acid is obtained by esterifying the optically active amino-acid preferably with methanol, ethanol or iso-propanol in the presence of gaseous HCl.

The ester is then isolated in the form of ester hydrochloride.

Subsequently:

(i) the ester hydrochloride is dissolved in $H_2O$, the pH is brought to neutrality with a saturated basic solution, e.g. a $Na_2CO_3$ solution; the solution thus obtained is repeatedly extracted with methylene chloride, chloroform or ethyl ether, the organic phase is dried, concentrated and the ester of the optically active amino-acid is isolated as free base and used as such in the reaction with the halogenide of the carnitine acylderivative (Process A), respectively with carnitine or acyl-carnitine (Process B); or:

(ii) the ester hydrochloride is suspended in ethyl ether and triethylamine or pyridine in equimolar amounts is added at 0° C.; the triethylamine or pyridine hydrochloride thus formed is filtered off, the ether solution is concentrated and the ester of the optically active amino-acid, isolated as free base, is used as such for the condensation with the halogenide of carnitine or carnitine acyl derivative (step (c) of Process A) or with carnitine or acyl-carnitine (step (a') of Process B).

Process A and B for preparing the amides of formula (I) are illustrated in the following synthesis scheme:

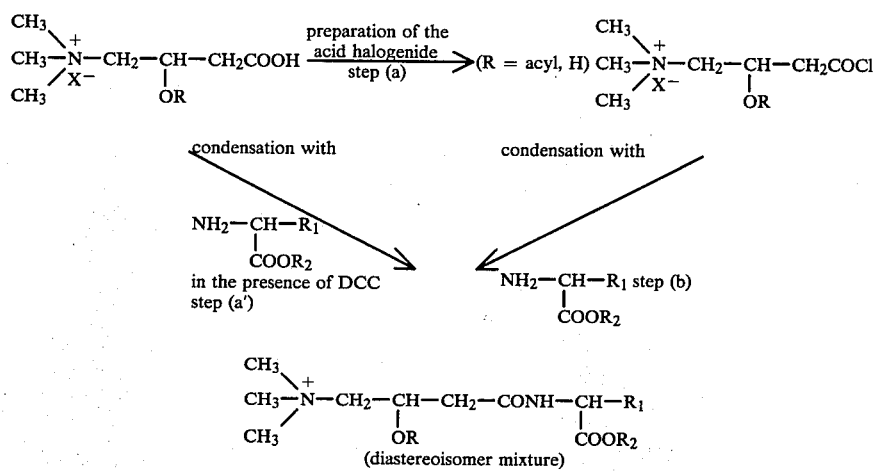

The amide of formula (I), as obtained with the foregoing processes, is actually a mixture of diastereoisomer amides. For instance, by reacting acetyl-D,L-carnitine with either one of the two optically active forms of the glutamic acid (diester), the following diastereoisomers (wherein the asymmetrical carbon atoms are marked with the asterisk) will be obtained:

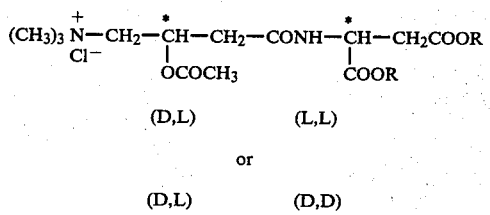

depending on whether the utilized glutamic acid (diester) is in its laevorotatory or dextrorotatory form.

In order to achieve the resolution of the mixture of amides of general formula (I) thus isolating the separate diastereoisomers, the mixture is subjected to fractional crystallization wherefor a solvent agent/precipitating agent mixture is used. Suitable mixtures are acetone-/ethyl acetate and methanol/acetone.

The solid phase which precipitates out substantially consists of one of the diastereoisomers, whereas the liquid phase substantially comprises the other diastereoisomer. Practically pure isomers can be obtained by repeated crystallizations.

The relative amounts of solvent agent to precipitating agent depend on the specific amide and the concentration of the isomers to each other. These correlated amounts of solvent agent and precipitating agent will be easily determined by any expert, having in mind that in order to achieve the best resolution, the least necessary amount of solvent and the least amount of precipitating agent which causes a thin opalescence to form, will be suitably used.

The following non-limiting examples aim at illustrating the preparation of some amides of this invention.

EXAMPLE 1

Preparation of the acetyl-carnitinamide of L-glutamic acid isopropyl diester (Process A)

(a) Preparation of the acid chloride of D,L-acetyl carnitine

To acetyl carnitine hydrochloride (1.2 g; 0.005 moles) oxalyl chloride (2.5 ml; 0.029 moles) was added and the resulting mixture was kept under stirring at room temperature for 2 hours. The mixture was then dried under vacuum, the residue was washed three times with anhydrous ethyl ether, thus obtaining the acid chloride of acetyl carnitine which was used as such in the next step.

(b) Condensation of the acid chloride of D,L-acetyl carnitine with L-glutamic acid isopropyl diester A suspension of the previously prepared acid chloride (0.005 moles) in 20 ml of anhydrous methylene chloride was slowly added under stirring to the L(+) glutamic acid isopropyl diester free base $[\alpha]_D = +19$ (1.3 g; 0.005 moles) dissolved in 20 ml of anhydrous methylene chloride. The reaction mixture was kept at room temperature under stirring for 3 hours and then dried. The residue was taken up with anhydrous isopropanol and the unreacted acetyl carnitine was precipitated with anhydrous ethyl ether. The solution was concentrated and the resulting residue was washed with $H_2O$ which has been previously cooled to 0° C., in order to eliminate the unreacted glutamic acid isopropyl diester. The residue (presumably, a mixture of the two diastereoisomers) was analyzed by TLC (silica gel; eluant $CHCl_3$ 55, $CH_3OH$ 35, $NH_4OH$ 5, $H_2O$ 5) and turned out to consist of 2 spots, the first one at $R_f$=higher and the second one at $R_f$=lower.

(c) Resolution of diastereoisomers

The product having lower $R_f$ with $[\alpha]_D = -10$ (1% H₂O) was isolated by repeated crystallizations with acetone-ethyl acetate. In the mother liquors the concentration of the product at higher $R_f$ increased. By NMR analysis of the product at lower $R_f$ it was confirmed that the isolated compound was acetyl-carnitinamide of the glutamic acid isopropyl diester.

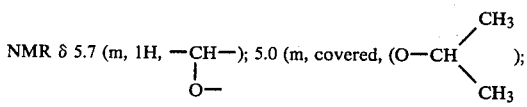

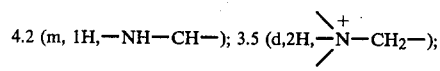

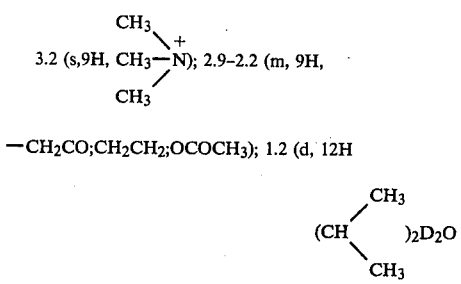

—CH₂CO;CH₂CH₂;OCOCH₃); 1.2 (d, 12H

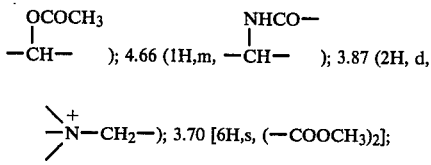

A comparison sample of L-acetyl carnitinamide of the L-glutamic acid isopropyl diester was prepared with the same process as that outlined above, using pure L-acetyl carnitine hydrochloride $[\alpha]_D = -27$ (1% H₂O). The product thus obtained showed $[\alpha]_D = -17$ (1% H₂O).

(d) Hydrolysis of the amide bond on the isolated diastereoisomer

The diastereoisomers, isolated as previously described in step (b), was dissolved in H₂O and to the resulting solution oxalic acid (amide: oxalic acid ratio = 1:3) was added. The solution was kept at reflux temperature for about 7 hours, then filtered and the filtrate concentrated to dryness. The residue consisting of L-carnitine was passed through IRA 402 resin (activated in OH form) to eliminate any trace of oxalic acid. The eluate was acidified up to pH 2 with conc. HCl and subsequently lyophilized. The lyophilized product consisting of L-carnitine (as checked by TLC and NMR analysis) showed $[\alpha]_D = -20$ (1% H₂O).

EXAMPLE 2

Preparation of carnitinamide of L (+) aspartic acid dimethyl ester (Process B)

(a') Condensation carnitine/L (+) aspartic acid dimethyl ester in the presence of DCC Triethylamine (4.2 ml; 0.03 moles) was added to a solution of L (+) aspartic acid dimethylester · HCl (6 g; 0.03 moles) in acetone (200 ml). The mixture was kept 0.5 hours under magnetic stirring at room temperature. The precipitate of triethylamine · HCl which separated was filtered off. To the filtered solution was added under magnetic stirring and at room temperature a solution of dicyclohexylcarbodiimide (7 g; 0.03 moles) in acetone (100 ml) and D,L-carnitine hydrochloride (6 g; 0.03 moles) dissolved in 10 ml of H₂O. The reaction mixture was kept under stirring overnight.

(b') Isolation of the diastereoisomer mixture

The precipitate thus formed (dicyclohexylurea) was filtered off. The filtrate was concentrated under vacuum till complete acetone evaporation. The residual aqueous solution was washed three times with small amounts of CHCl₃ (to eliminate any residue of the starting ester and triethylamine still present). Then, the aqueous phase was evaporated to dryness. The raw product, analyzed by TLC (CHCl₃, MeOH, H₂O, NH₄OH 55:35:5:5, silica gel), consisted of two spots having $R_f$ close to each other.

$[\alpha]_D$ (raw material) = $-8.2$ (1% in H₂O) [mixture of the two diastereoisomers].

The NMR (DMSO) analysis showed two doublets in the δ range 9.15–8.72, one whereof representing the 70% (calculated on the integral).

(c') Resolution of the diastereoisomers

The two diastereoisomers were risolved by fractional crystallization from methanol-acetone. The product having lower $R_f$ was the first to crystallize out whilst the mother liquors became richer in the product at higher $R_f$. By a series of four crystallizations it was possible to obtain the pure diastereoisomer at lower $R_f$, which was a highly hygroscopic and deliquescent substance. $[\alpha]_D = -13.5$ (1% in H₂O).

NMR (DMSO), δ: 9.00 (1H,d, —NHCO—); 5.60 (1H,m,

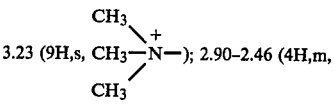

—CH₂—COOCH₃/—CH₂—CONH—) 2.10 (3H,s, —OCOCH₃);

In order to check the foregoing data, the amide of the L (+) aspartic acid dimethyl ester was prepared from a sample of pure L (−) carnitine hydrochloride following the same procedures as those hereinabove described.

The product thus obtained showed the same chemicophysical characteristics of the previously isolated diastereoisomer having lower $R_f$. This product had $[\alpha]_D = -15$ (1% in H₂O).

(d') Hydrolysis of the amide group on the isolated diastereoisomer

A solution of the previously prepared amide (2 g; 0.006 moles) in 15 ml of H₂O and oxalic acid (1.8 g; 0.02 moles) was kept for 6 hours at the reflux temperature, then cooled and allowed to stand in a refrigerator overnight. The reaction mixture was filtered and the filtrate washed three times with CHCl₃, then evaporated to dryness.

The residue, taken up with MeOH, filtered and precipitated with CH₂Cl₂, yielded raw L (−) carnitine. This product was dissolved in water and passed through IRA 402 resin (strongly anionic resin) and eluted with H₂O, then acidified with HCl 6 N and lyophilized.

This lyophilized L (−) carnitine showed [α]$_D$=−23 (1% H₂O).

EXAMPLE 3

Preparation of acetyl carnitinamide of phenylglycine ethylester (Process A)

10 g of phenylglycine were added to 150 ml of absolute ethanol. Gaseous HCl was bubbled at room temperature under stirring in the resulting solution, until all of the phenylglycine was dissolved. The solution was kept at reflux temperature overnight, then cooled and dried under vacuum. The residue was again dissolved in H₂O and the resulting solution neutralized with NaHCO₃. The phenylglycine ethylester free base was extracted with CH₂Cl₂.

A solution of acetyl carnitine hydrochloride (10 m moles in CH₂Cl₂) prepared as shown in Example 1 was added to a solution of 1.8 g (10 m moles) of phenylglycine ethylester free base dissolved in 10 ml of CH₂Cl₂. The mixture was kept under stirring overnight at 50° C. and then cooled. Ethyl ether (50 ml) was added to the mixture.

The oil which formed was dissolved in an ethanol-:acetone (5:1) mixture and precipitated again with ether.

NMR (DMSO) δ =

1.1 (t, 3H, —CH₂—CH₃); 2.0 (s, 3H, —CO—CH₃);

2.8 (d, 2H,—CH₂—CO—); 3.2 (s, 9H,—(CH₃)₃—N);

3.5 (d, 2H, —N—CH₂); 4.0 (q, 2H,—CH₂—CH₃);

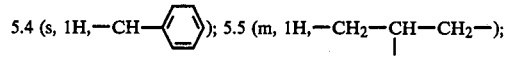

Elementary analysis: calculated: C=56.92; H=7.29; N=6.99; Cl=8.84; found: C=56.84; H=7.31; N=6.89; Cl=8.72.

EXAMPLE 4

Preparation of the acetyl carnitinamide of the leucine methyl ester

The acetylcarnitinamide with leucine methyl ester was prepared by following the procedures of Example 1. The NMR analysis of the product thus obtained showed the following results:

δ 8.8 (d, 1H, —NHCO—); 5.5 (m, 1H, —CH—); | O 4.4 (m, 1H, —NH—CH—); 3.8 (m, 5H, \+N—CH₂, —OCH₃);

3.2 (s, 9H, CH₃—\+N(CH₃)—); 2.9 (d, 2H, —CH₂CO—);

2.2 (s, 3H, —COCH₃); 1.5 (m, 3H, CH₂—

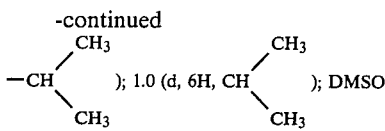

L-leucine [α]$_D$=+12 (2.5% HCl 1 N).
L-leucine methyl ester hydrochloride [α]$_D$=−13.4 (c=5% H₂O).

EXAMPLE 5

Preparation of the acetyl carnitinamide of isoleucine methylester

The acetyl carnitinamide with isoleucine methyl ester was prepared by following the procedures of example 2. The NMR analysis of the product gave the following results:

8.7 (d, 1H, —NHCO—); 5.5 (m, 1H, —CH—); | O 4.3 (m, 1H, —NH—CH); 3.9 (s, 9H, \N—NCH₂);

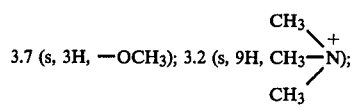

2.7 (covered, —CH₂—CO—); 2.1 (s, 3H, —COCH₃); 1,4 (m, 3H,

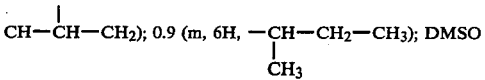

L isoleucine [α]$_D$=+35 (c=5% HCl 1 N).
L isoleucine methyl ester hydrochloride [α]$_D$=+26.6 (c=2% H₂O).

EXAMPLE 6

Preparation of the acetyl carnitinamide of the valine methyl ester

Acetyl carnitinamide with valine methyl ester was prepared by following the procedures of Example 2. The NMR analysis of the product gave the following results:

5.7 (m, 1H, —CH—); 4.4 (m, 1H, NH—CH—); 3.8 (m, 5H, | O

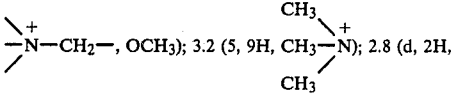

—CH₂—CO—); 2.2 (s, 3H, —COCH₃); 1.3-0.9 (m, 7H,

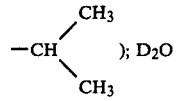

L-valine methyl ester hydrochloride [α]$_D$=+15.5 (c=2% H₂O).
L-valine [α]$_D$=+24 (c=5% HCl 1 N).

EXAMPLE 7

Preparation of carnitinamide of L-methionine methylester (Process B)

L-methionine methyl ester free base was prepared from its hydrochloride dissolved in acetone by adding an equivalent amount of triethylamine (as described in connection with aspartic acid dimethyl ester).

Methionine methyl ester free base (1.95 g; 0.01 moles) was suspended in a 1:1 acetone/dioxane mixture (50 cc) and added with a solution of dicyclohexyl carbodiimide (7 g; 0.03 moles) in dioxane (100 cc) and a solution of D,L-carnitine hydrochloride (1.97 g; 0.01 moles) in $H_2O$ (5 cc).

The reaction mixture was kept under stirring for 24 hours at room temperature. The precipitate of dicyclohexylurea which formed was filtered off. The solution was concentrated to dryness. The residue, analyzed by TLC ($CHCl_3$:MeTOH:$CH_3$ COONa 0.01 M; 40:40:10) was shown to consist of two products having $R_f$ very close to each other (developing agent: iodine).

By repeated crystallizations with acetone-acetonitrile the product at lower $R_f$ was isolated and consisted of the L-carnitinamide of L-methionine methyl ester.

NMR DMSO δ 8.8 (d, 1H, —CONH—); 4.5 (m, 1H, —CH—);
|
O 4.3 (t, 1H, —CH—); 3.8 (m, 5H, —COOCH$_3$,N—CH$_2$—); 3.2 (s,
|
NH—

9H, CH$_3$N); 2.7 (covered by DMSO,—CH$_2$CO—,
CH$_3$

—CH$_2$S—); 2.2 (t, 2H, —CH$_2$—CH); 2.1 (s, 3H, —CH$_3$—S—)

Hydrolysis of the amide bond of the isolated diastereoisomer

The previously isolated amide (3.4 g; 0.01 moles) was dissolved in a 2 M solution of oxalic acid in $H_2O$ (15 cc). The solution was heated up 55° C. for 10 hours. Then, the solution was cooled and 50 cc of ethanol were added thereto. The resulting mixture was kept at 0° C. overnight. The precipitate which formed was filtered off and the aqueous solution was concentrated in order to remove the alcohol. The concentrate was taken up with water and the solution was passed through IRA 402 Amberlite resin (strongly anionic resin). The eluate was lyophilized.

The lyophilized product, analyzed by TLC and NMR, was shown to consist of L-carnitine inner salt. $[\alpha]_D = -20$ (c=1% $H_2O$).

EXAMPLE 8

Preparation of carnitinamide of L(+) alanine ethyl ester (Process A)

A solution of L(+) alanine ethyl ester hydrochloride in $H_2O$ was passed through a weakly anionic resin (Amberlite IR 45). The eluate was lyophilized to obtain L(+) alanine ethyl ester free base $[\alpha]_D = +4$ (c=2% in HCl 5 N).

L(+) alanine ethyl ester free base (1.5 g; 12.5 moles) was dissolved in methylene chloride and to the resulting solution was slowly added under stirring, at room temperature a solution of the acid chloride of D,L acetyl carnitine (12.5 m moles, prepared as previously described). The solution was kept at 40° C. overnight. After cooling to 0° C., the solution was filtered and to the filtrate ethyl ether was added, thus obtaining and oil.

This oily residue was purified by dissolving it in $H_2O$, treating the aqueous solution with Amberlite XAD$_2$ and lyophilizing. The lyophilized product, hypothesized to be the mixture of the two diastereoisomers, was analyzed by TLC ($CHCl_3$ 55, $CH_3OH$ 55, $NH_4OH$ 5, $H_2O$ 5; development: Dragendoff's reagent) and was shown to consist of two products, at higher $R_f$ and lower $R_f$, respectively. NMR in DMSO δ9-8.8 multiplet caused by the presence of the two amides.

Repeated crystallizations were carried out with a mixture of solvents: methylene chloride, acetone and ethyl acetate thus isolating the product at lower $R_f.[\alpha]_D = -8$.

NMR DMSO δ 8.9 (d, 1H, —CONH—), 5.5 (m, 1H, —CH—);
|
O 4.3-3.5 (m, 5H, —CH$_2$CH$_3$; N—CH$_2$; —CH—); 3.2 (s, 9H,
|
NH CH$_3$
CH$_3$—N); 2.7 (covered by DMSO,—CH$_2$CO); 2.1 (s,
CH$_3$ 3H, —COCH$_3$); 1.5 (t, 3H, CH$_3$CH$_2$—)

The hydrolysis of the amide bond of the ester on the isolated diastereoisomer and L-carnitine isolation were carried out as previously described for the acetyl carnitinamide with the isopropyl diester of the glutamic acid.

The isolated L-carnitine (corresponding TLC and NMR) showed $[\alpha]_D = -19$ (1% $H_2O$).

As previously mentioned, the amide of general formula (I) are useful therapeutic agents for the treatment of cardiac disorders, hyperlipidaemias and hyperlipoproteinaemias.

They can also be used for obtaining, starting from D,L-carnitine or an acyl-D,L-carnitine (e.g. acetyl D,L-carnitine) the separated D and L isomers, respectively. The usefulness of resolving the optical isomers of carnitine is brought about insofar as the L form and the D form exhibit different, and sometimes reciprocally antagonizing, therapeutical actions.

A process for preparing L-carnitine hydrochloride and D-carnitine hydrochloride is disclosed in the Belgian Patent 660039. According to this process, D,L-carnitine hydrochloride is converted into D,L-carnitinamide hydrochloride, which is reacted with silver D-camphorate, thus forming the D-camphorate of D,L-carnitinamide. By fractional crystallization from an alcoholic solution, preferably an isopropanol solution, of D-camphorate of D,L-carnitinamide is obtained the D-camphorate of L-carnitinamide which is the first fraction to crystallize out of the solution. L-carnitine hydrochloride is then obtained with conventional hydrolysis procedures from the D-camphorate of L-carnitinamide.

This process entails the serious drawback, which makes it seldom applicable on an industrial scale, that silver D-camphorate is necessarily used. Silver D-camphorate is obtained by firstly reating D-camphoric acid with ammonia and then reacting the ammonium D-camphorate thus obtained with silver nitrate. Since D,L-carnitinamide is in the form of a hydrochloride salt; the formation of the silver salt aims at removing the chloride ion. As a consequence of the use of the silver nitrate, this process is expensive and cumbersome insofar as the various process steps must be carried out away from light in order to prevent darkening of reactors, because of the large amounts of silver chloride which form. Moreover, the final product might be contaminated by the presence of silver ions.

In order to overcome these serious drawbacks and particularly to totally eliminate the use of silver salts, in the Italian Patent application Ser. No. 50222 A/78 corresponding to U.S. Pat. No. 4,254,053 a process has been disclosed wherein D,L-carnitinamide free base (obtained by passing a D,L-carnitinamide hydrochloride solution through an ion-exchange resin column) is directly reacted with D-camphoric acid, thus giving the D-camphorate of D,L-carnitinamide. Although this process represents a remarkable improvement over the process of the foregoing Belgian Patent, according to the process of the Italian patent application No. 50222 A/78 it is still necessary to react the carnitinamide with a suitable resolution agent (i.e. the D-camphoric acid) which subsequently must be removed.

Conversely, the amides of the present invention present the advantage that they can be directly resolved into their diastereoisomers by fractional crystallization from alcoholic solvents. That is, these amides allow the separation of L-carnitine from D-carnitine to be achieved not only avoiding the silver salt use, but also without any resolution agent, such as D-camphoric acid, being resorted to.

What is claimed is:

1. Carnitinamide having formula:

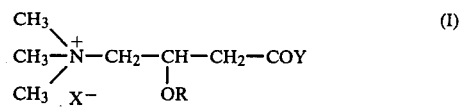

wherein:

X is a halogen anion;

R is either hydrogen or an acyl radical selected from the group comprising acetyl, propionyl and butyryl;

Y is the residue of an optically active, esterified amino-acid having formula:

wherein
$R_1$ is:
—$CH_2COOR_2$
—$(CH_2)_2COOR_2$
—$CH_2S_2CH_2CH(NH_2)COOR_2$
—$CH_3$
—$CH(CH_3)_2$
—$CH_2CH(CH_3)_2$
—$CH(CH_3)CH_2CH_3$
—$(CH_2)_2SCH_3$
—$C_6H_5$
—$CH_2C_6H_5$
—$CH_2CONH_2$
—$(CH_2)_2CONH_2$

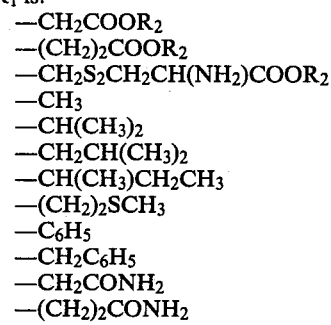 and

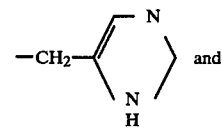

$R_2$ is: an alkyl radical having 1 to 4 carbon atoms.

2. The amide of claim 1, wherein said aminoacid is an L-aminoacid.

3. The amide of claim 2, wherein the residue of the esterified L-aminoacid is the residue of the isopropyl diester of the L-glutamic acid, the methyl diester and ethyl diester of L-aspartic and L-cystine; the methyl ester and ethyl ester of L-asparagine, L-phenylalanine, L-glutamine, L-phenylglycine, L-leucine, L-isoleucine, L-methionine, L-histidine, L-valine and L-alanine.

* * * * *